United States Patent
Shiraishi

[11] 3,948,087
[45] Apr. 6, 1976

[54] VIBRATION APPARATUS FOR MINUTE VIBRATIONS

[75] Inventor: Kenji Shiraishi, Ohmiya, Japan

[73] Assignee: Agency of Industrial Science & Technology, Tokyo, Japan

[22] Filed: Oct. 1, 1974

[21] Appl. No.: 511,058

[30] Foreign Application Priority Data
Oct. 5, 1973    Japan.............................. 48-111509

[52] U.S. Cl. ................................................. 73/71.6
[51] Int. Cl.² ......................................... G01N 29/00
[58] Field of Search......... 73/71.6, 71.5 R, 67, 67.2, 73/DIG. 1, 1 DV

[56]    References Cited
UNITED STATES PATENTS

| | | | |
|---|---|---|---|
| 3,393,555 | 7/1968 | Flannelly | 73/71.6 |
| 3,597,960 | 8/1971 | Otera | 73/71.6 X |
| 3,693,400 | 9/1972 | Savit | 73/1 DV |
| 3,710,082 | 1/1973 | Sloane et al. | 73/71.6 |

*Primary Examiner*—Richard C. Queisser
*Assistant Examiner*—Stephen A. Kreitman
*Attorney, Agent, or Firm*—Oblon, Fisher, Spivak, McClelland & Maier

[57]    ABSTRACT

An electro-dynamic shaker and a pendulum system which has a resonant frequency lower than the lower limit of the frequency band of ordinary floor vibrations are fixedly mounted on a base plate. The pendulum system comprises a pendulum, damper and a differential transformer for detecting the relative displacement between the pendulum and the output shaft of the shaker. The detected relative displacement is compared in a control device with an input signal, the difference obtained by the comparison being used as a negative feedback signal to correct the input signal to be fed to the shaker to thereby stably produce minute vibration.

11 Claims, 5 Drawing Figures

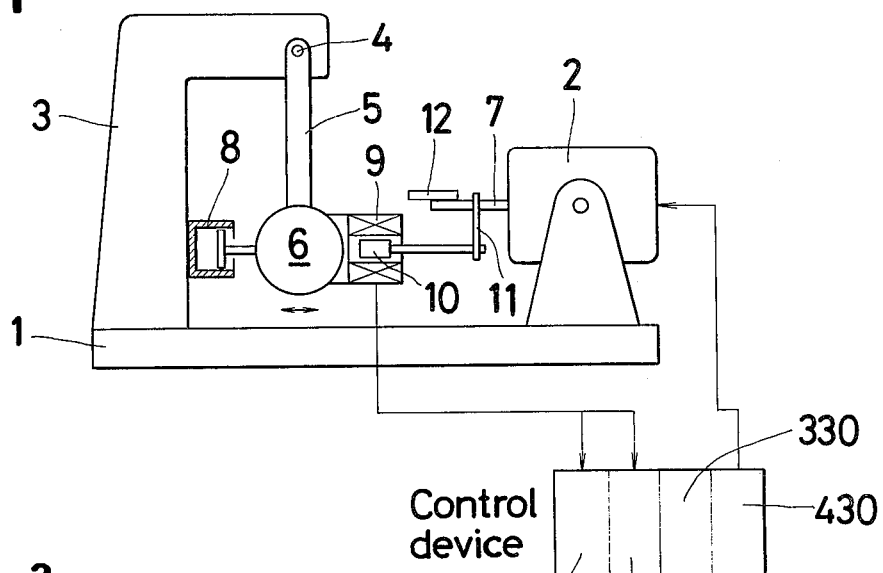
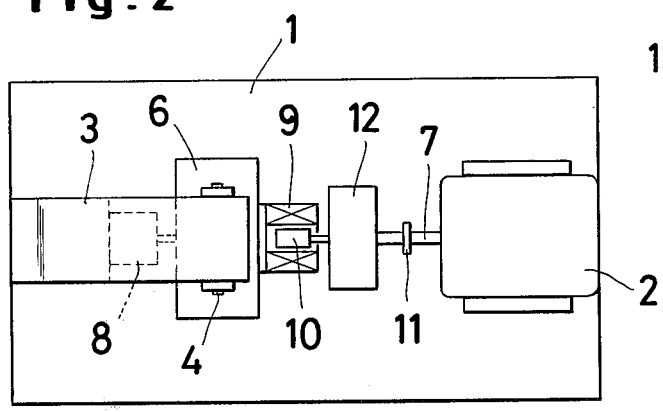
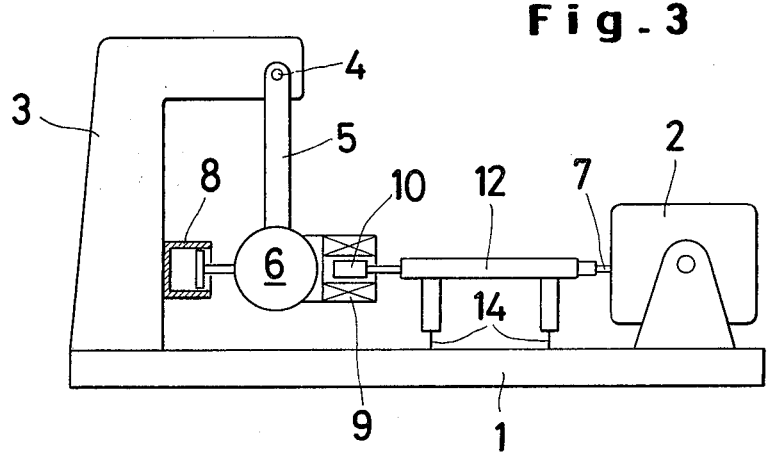

VIBRATION APPARATUS FOR MINUTE VIBRATIONS

BACKGROUND OF THE INVENTION

The present invention relates to a vibration apparatus for producing minute vibrations. More particularly, the present invention relates to a vibration apparatus for producing minute vibrations for use in testing the effect of such vibrations on precision measuring devices.

In general, the floor of a room on which a measuring device is disposed is always subjected to extraneous minute vibrations. The frequency of such vibrations is, in general, within a range from 1 to 50 Hz and the amplitude thereof is very small, being less than about 10 $\mu$m. Even so, such vibration of the floor causes measuring devices disposed thereon to vibrate also. Therefore, when the measured value is to be highly amplified, it becomes difficult to obtain a precise measurement because extraneous floor vibrations influence the measured value. Accordingly, when the measured value is to be highly amplified, it is desirable to know the extent to which extraneous floor vibrations affect the reading of the measuring device.

To determine the influence of floor vibrations on the reading of the measuring device, it is sufficient to know the relationship between the floor vibrations and the reading of the measuring device. However, the frequency spectrum of floor vibrations is generally within the range from 1 to 50 Hz. The vibrations, however, are not generally spread uniformly over this frequency band but are often concentrated within a very narrow range. Therefore, the above mentioned relationship cannot easily be determined for frequencies outside this narrow range. In order to overcome this problem, a vibration test using a vibration apparatus becomes necessary. However, conventional vibration apparatuses are designed for use in testing equipment for resistance to vibration and are therefore capable of producing large-amplitude or high-acceleration vibrations. Thus when such an apparatus is used to produce a very small vibration (minute vibration), it is very difficult to produce a vibration having a desired waveform because of the influence of the minute vibrations of the floor upon which the apparatus stands. To overcome this problem, the vibration test may be performed at a large amplitude and large acceleration. In this case, however, although the vibration of the floor will become relatively negligible, the measuring device itself will be put under much different conditions from the normal desired conditions. This leads to two obvious disadvantages. First, it is difficult to theoretically determine the effect of the vibrations to which the apparatus is subject in normal use from the effect of the vibrations used in the test because of the non-linearity of the parameters in such test employing large amplitude and large acceleration. Second, there is a possibility of damage to the apparatus itself. Therefore, in order to measure the effect of vibrations on the reading of the measuring device, it is preferrable to test the device using minute vibrations similar to floor vibration. For this reason, there is required a vibration apparatus which can provide minute vibrations simulating floor vibration without itself being influenced by extraneous floor vibrations.

Accordingly, the object of the present invention is to provide a vibration apparatus which can readily produce minute vibrations in simulation of any type of floor vibration.

SUMMARY OF THE INVENTION

In order to achieve the above object, the vibration apparatus according to the present invention comprises a base structure, a vibrator or shaker secured to the base plate, a pendulum also mounted on the base plate and having a resonant frequency lower than the frequency band of the extraneous floor vibration, a differential transformer mounted on the pendulum for measuring the displacement of the pendulum due to the extraneous floor vibration with respect to an output shaft of the shaker and producing an electric signal proportional to the measured relative displacement and a control means responsive to said electric signal to feed it back to the shaker for modifying the displacement thereof by an amount equal to the displacement due to the floor vibration to thereby automatically control the displacement of the output shaft of the shaker to cause it to produce a desired vibration waveform. Therefore, the vibration apparatus according to the present invention can exactly and readily produce a minute vibration similar to a floor vibration.

Other objects and features of the present invention will become clear from the following description of preferred embodiments of the present invention with reference to the attached drawings.

SUMMARIZED EXPLANATION OF THE DRAWINGS

FIG. 1 is a side view of an embodiment of the vibration apparatus for producing minute vibrations according to the present invention;

FIG. 2 is a plan view of the apparatus shown in FIG. 1;

FIG. 3 to FIG. 5 are side views of other embodiments of the present invention.

DESCRIPTION OF THE EMBODIMENTS

Figure 4:
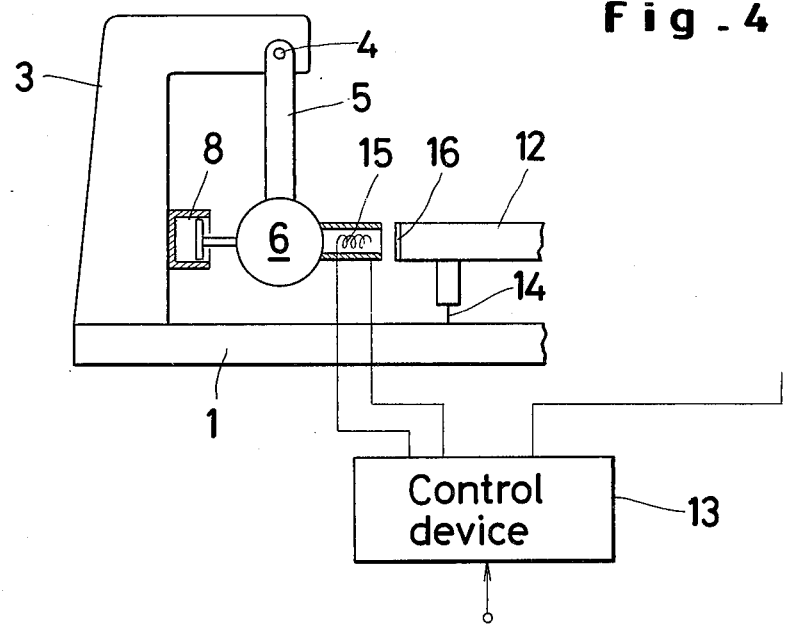

Returning to the drawings, in particular, to FIGS. 1 and 2, a base plate 1 has mounted fixedly thereon an electro-dynamic type shaker 2 and a stand 3 which supports, at a fulcrum 4, a pendulum 5 in a freely swingable state in the horizontal plane. The weight 6 of the pendulum 5 and the output shaft 7 of the shaker 2 are arranged so that they can vibrate in the same direction. The length and weight of the pendulum 5 itself together with the weight 6 thereof are selected in such a manner that the resonant frequency of the pendulum 5 becomes lower than the frequency band of the floor vibration (normally, from 1 to 50 Hz). For this reason, a floor vibration causes a relative displacement between the support point 4 and the weight 6 approximating the displacement of the support point 4, so that the weight 6 is held in an approximately steady state. In this case, however, in order to prevent the pendulum 5 from vibrating at its resonant frequency, a damper 8 which may be of any of well-known type, such as the viscous, hydraulic, oil or electromagnet type, is provided between the weight 6 and the stand 3. A differential transformer 9 is also provided on the weight 6 of the pendulum 5 to detect the relative displacement thereof with respect to the output shaft 7 of the shaker in a non-contact manner. The core 10 of differential transformer 9 is mechanically connected through an arm 11 to the output shaft 7 of the shaker 2. There is provided fixedly, at the top portion of the output shaft 7, a table 12 on which the measuring apparatus or other device to be tested is mounted.

A control device 13 is electrically connected to the differential transformer 9 which detects the relative displacement between the output shaft 7 of the shaker 2 and the weight 6 of the pendulum 5 occurring as a result of floor vibrations, etc. A signal proportional to the relative displacement detected by the differential transformer 9 is thus received by control device 13 which then modifies the input signal to be supplied to the shaker 2 by an amount corresponding to the detected displacement so as to automatically control the shaker. Accordingly, components of the floor vibration are prevented from being transmitted to the output shaft of the shaker.

In the vibration apparatus of the above construction, assume that there is no input signal to the shaker and only floor vibration is applied thereto. In this case, the pendulum 6 is held in the steady state and the floor vibration affects only the shaker. Therefore, the motion of the shaker due to the floor vibration is detected by the differential transformer through the output shaft and the core and the displacement thus detected is converted by the control device to a signal proportional to the measured displacement. This latter signal is feedback to the shaker so that the shaker is automatically controlled so that the relative positional relation between the core of the differential transformer and the weight of the pendulum is instantaneously maintained in the desired state.

Then, when an input signal of suitable size to cause the shaker 2 to produce a desired vibration amplitude is supplied to the shaker 2 through the control device 13 which will be described in detail later, a vibration which is an addition combination of the above-mentioned floor vibration component and the input signal component is produced on the output shaft 7 thereof.

The control device 13 comprises a first circuit section 130 for suitably amplifying the output signal of the differential transformer 9, a second circuit section 230 for differentiating the output of the differential transformer 9, circuit section 330 for comparing the input signal having a desired value with the summation of the output of the first circuit section 130 and the output of the second circuit section 230 and producing an output equal to the difference therebetween and a fourth circuit section 430 for suitably amplifying the difference to produce a driving signal representative of the manipulated variable of the electro-dynamic shaker 2.

The signal proportional to the relative displacement between the weight 6 of the pendulum 5 which is held in the steady state and the output shaft 7 of the shaker 2 is compared in the comparing circuit section 330 and modified so that a desired displacement is obtained by taking account of the driving characteristics of the shaker 2 to drive it and to produce the desired vibration on the output shaft 7 thereof. In order to produce a damping force for preventing the shaker 2 from becoming unstable due to this control, the signal proportional to the relative displacement of the shaft 7 with respect to the weight 6 of the pendulum 5 is compared with the input signal after being addition-combined with another signal proportional to the relative velocity of the output shaft 7 with respect to the weight 6 of the pendulum 5 which is obtained by differentiating, in the control device, the signal proportional to the relative displacement.

Since, in this manner, the input signal which is constantly modified according to the varying floor vibration is fed to the shaker continuously, it becomes possible to reproduce the desired very small amplitude vibration stably on the table 12.

As precision measuring devices delicately responsive to very small amplitude vibration, which can be tested by using the vibration apparatus constructed according to the present invention, there can be mentioned are shape measuring machines, surface roughness testers, flatness measuring interferometers, roundness measuring machines, balances, straightness measuring machines etc. In case where the measuring device to be put on the table is so large as to make the positioning thereof on the table difficult, a modification of the apparatus in FIGS. 1 and 2 is effectively usable. This modification is shown in FIG. 3 wherein the table 12 is provided with legs which are fixed to the base plate 1 through leaf springs 14. The table 12 is directly connected between the output shaft 7 of the shaker 2 and the core 10 of the differential transformer 9. With the arrangement shown in FIG. 3, the same effect as that obtained by the construction in FIGS. 1 and 2 is obtained. That is, the minute vibrations from the floor are transmitted through the output shaft 7 of the shaker and the leaf springs 14 to the table 12. The displacement value of the table due to the transmitted vibration is simultaneously detected by the differential transformer and the shaker receives the input signal corrected by the control device 13 by an amount corresponding to the displacement. Therefore, only the desired vibration is reproduced on the table 12.

FIG. 4 shows another embodiment of the minute vibration apparatus of the present invention. In FIG. 4, instead of the differential transformer, a coil 15 is fixed on the weight 6 and a metal piece 16 is fixed on the table 12 at a position facing the coil 15. Therefore, under application of high frequency electric power to the coil 15, the impedance of the coil is constant when the distance between the coil and the metal piece is constant and is varied according to the variation in distance. The control device 13 determines whether the impedance variation corresponds to the variation in the desired vibration amplitude to be produced by the shaker upon receiving the input signal, and, if not, the input signal is corrected by an amount corresponding to the difference and the corrected signal is fed to the shaker to produce the desired minute vibration on the table 12.

In the last mentioned embodiment, the coil 15 is fixed on the weight of the pendulum. It should be recognized, however, that the coil may be fixed on the table 12 or, in FIG. 1, it is possible to mount it on the output shaft 7 of the shaker 2.

The embodiments described hereinbefore are suitable for producing the vibrations in the horizontal direction. The present invention can also be used to produce vibration in the vertical directions.

Figure 5:
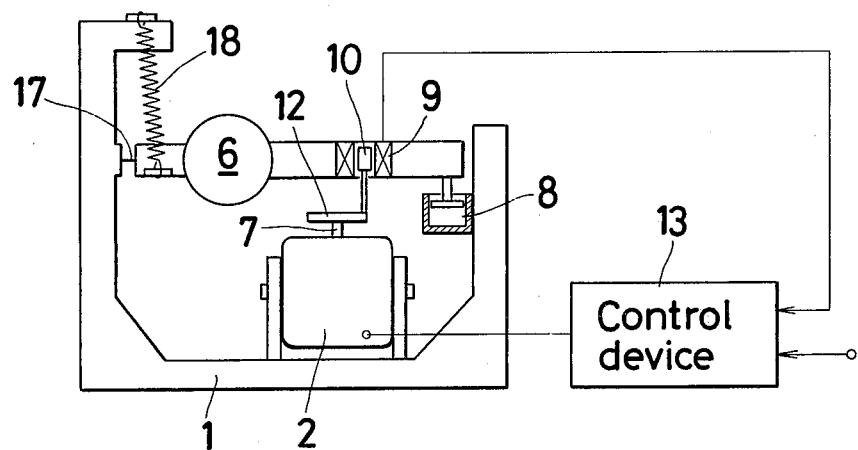

Referring to FIG. 5, the electro-dynamic shaker 2 is fixedly mounted on the base plate 1 so that the output shaft 7 thereof can vibrate in the vertical direction. The table 12 on which the precision measuring device is to be put is secured to the top end of the output shaft 7. The pendulum 5 is regulated so that it has a resonant frequency such that it remains steady even when a vibration of a frequency near the bottom of the frequency band of the floor vibration is applied to the pendulum. One end of the pendulum at which the weight 6 is mounted is supported by a leaf spring 17 and a helical spring 18 and the other end is supported by the damper 8. If the leaf spring 17 has stiffness enough to maintain a constant resiliency coefficient, the spring 18 may be omitted. The pendulum 5 is provided with the differential transformer 9 and the core 10 inserted therein is supported by the table 12.

When a vertical floor vibration is applied to the vibration apparatus of FIG. 5, the pendulum 5 is held in a steady state. However, the core 10 of the differential transformer 9 vibrates in response to the vertical vibration and the differential transformer detects the vibration of the core 10. The detected displacement of the core is converted by the control device into a signal proportional thereto by which the input signal is modified. The modified input signal is supplied to the shaker to automatically control the position of the core and the pendulum so that they are shifted instantaneously to desired positions to thereby produce only the desired vibration on the table. It will be noted that this circuit construction completes a negative feedback loop.

As will become clear from the foregoing, since according to the present invention, arbitrary small vibrations simulating the floor vibration can easily be produced in a state where the influence of floor vibrations is eliminated, it becomes possible to exactly determine the influence of the minute vibrations on the measured value of the precision measuring device.

What is claimed is:

1. An electro-dynamic vibration apparatus comprising a stationarily supported electro-dynamic shaker having a horizontally extending output shaft, a stationarily supported pendulum system having a resonant frequency sufficiently dissimilar from the frequency of vibrations in the environment of said apparatus to constitute a reference vibration isolation element, a table mechanically connected to said output shaft of said shaker to receive a device to be vibration-tested thereon and a negative feedback loop provided between said pendulum system and said shaker.

2. An electro-dynamic vibration apparatus as set forth in claim 1, wherein said pendulum system comprises a pendulum having a weight and a position detecting means fixedly mounted on said weight.

3. An electro-dynamic vibration apparatus as set forth in claim 2, wherein said negative feedback loop comprises a control means electrically connected between said position detecting means and said shaker.

4. An electro-dynamic vibration apparatus as set forth in claim 1, wherein said position detecting means comprises a differential transformer and a core mechanically connected to said output shaft and inserted in said transformer.

5. An electro-dynamic vibration apparatus as set forth in claim 1, wherein said detecting means comprises a detection coil and a metal element disposed on said table and electro-magnetically engaged with said coil.

6. An electro-dynamic vibration apparatus as set forth in claim 1, wherein said table is fixedly disposed on said output shaft.

7. An electro-dynamic vibration apparatus as set forth in claim 1, wherein said table is disposed between said core and said output shaft, and further comprising spring means for supporting said table.

8. An electro-dynamic vibration apparatus as set forth in claim 3, wherein said control means comprises an amplifying section for amplifying the output signal from said differential transformer, a a section for differentiating the output signal from said differential transformer, a comparing section for comparing the input signal to be fed to said shaker with the summation of the amplified output signal and the differentiated output signal and a controlling section for producing a driving signal for said shaker.

9. An electro-dynamic vibration apparatus as set forth in claim 1, further comprising a damper means for producing a damping force against undesired movement of said pendulum system.

10. An electro-dynamic vibration apparatus comprising a stationarily supported electro-dynamic shaker having an upright output shaft, a horizontally supported weight means having a resonant frequency sufficiently dissimilar from the frequency of vibrations in the environment of said apparatus to constitute a reference vibration isolation element, said weight means being provided with a differential transformer and being movable in the vertical direction, a table fixed on the top of said output shaft, a core mechanically connected to said table and movable in said differential transformer and a negative feedback loop having a control means and connected between said differential transformer and said shaker.

11. An electro-dynamic vibration apparatus comprising shaker means for generating vibrations, an output means on said shaker means, support means rigidly attached to said output means for supporting a device to be vibration tested, a reference vibration isolation element having a resonant frequency sufficiently dissimilar from the frequency of vibrations in the environment of said apparatus to be isolated from said environmental vibrations, first and second displacement means for detecting and generating a signal as to the displacement between said output means and said reference vibration isolation element, said first means being vibrated with said output means and said second means being carried by said reference vibration isolation element without contacting said first means, and negative feedback means between said shaker means and said first and second displacement detecting means.

* * * * *